United States Patent [19]

Miller et al.

[11] Patent Number: 4,795,853

[45] Date of Patent: Jan. 3, 1989

[54] ISOPARAFFIN SYNTHESIS OVER CADMIUM CATALYSTS

[75] Inventors: Jeffrey T. Miller, Naperville, Ill.; Thomas D. Nevitt, Albuquerque, N. Mex.

[73] Assignee: Amoco Corporation, Chicago, Ill.

[21] Appl. No.: 81,657

[22] Filed: Aug. 3, 1987

Related U.S. Application Data

[63] Continuation-in-part of Ser. No. 925,721, Oct. 30, 1986, abandoned, which is a continuation of Ser. No. 536,680, Sep. 28, 1985, abandoned.

[51] Int. Cl.$^4$ .............................................. C07C 1/04
[52] U.S. Cl. ................................... 585/733; 585/639; 585/469; 518/728
[58] Field of Search ............... 518/728; 585/733, 640, 585/639, 469

[56] References Cited

U.S. PATENT DOCUMENTS

| | | | |
|---|---|---|---|
| 2,478,899 | 8/1949 | D'Ownlle | 518/728 |
| 4,294,725 | 10/1981 | Fraenkel et al. | 518/715 |
| 4,496,785 | 1/1985 | Miller et al. | 585/733 |
| 4,559,363 | 12/1985 | Miller et al. | 585/733 |

FOREIGN PATENT DOCUMENTS

| | | | |
|---|---|---|---|
| 300294 | 11/1928 | United Kingdom | 518/715 |
| 306471 | 9/1929 | United Kingdom | 518/728 |

*Primary Examiner*—Asok Pal
*Attorney, Agent, or Firm*—Nick C. Kottis; Robert E. Sloat; William H. Magidson

[57] ABSTRACT

A process for reacting synthesis gas in the presence of a cadmium-containing catalyst to selectively produce isoparaffin hydrocarbons is disclosed.

9 Claims, No Drawings

ISOPARAFFIN SYNTHESIS OVER CADMIUM CATALYSTS

This application is a continuation-in-part of the U.S. Application, Ser. No. 925,721, filed Oct. 30, 1986, which is a continuation of Application Ser. No. 536,680, filed Sept. 28, 1985, now both abandoned.

BACKGROUND OF THE INVENTION

1. Field of the Invention

This invention relates generally to the reaction between carbon monoxide and hydrogen, and more particularly concerns such reaction in the presence of a cadmium-containing catalyst.

2. Description of the Prior Art

British Pat. No. 300,294, to I. G. Farben discloses a process for producing hydrocarbons, alcohols and esters from synthesis gas with a catalyst comprising iron, nickel or cobalt, plus cadmium or thallium. A support for the catalyst in this process may be pumice or asbestos.

British Pat. No. 306,471 to the Selden Company discloses a process for producing hydrocarbons and alcohols from synthesis gas with a catalyst comprising base-exchange bodies or their derivatives. The base-exchange bodies in this process may be two-component zeolites or non-silicious bodies in which all of the silicon is replaced by other suitable acidic or amphoteric metal oxides. Catalytically active metal components may be added to the base-exchange bodies, and supports or diluents for the bodies may be kieselguhrs, silicious powders, lava, sand, activated charcoal, etc.

U.S. Pat. No. 2,478,899 to d'Ouville discloses a process for reactivating catalysts containing iron, nickel or cobalt, and magnesia, thoria or oxides of the alkaline earth metals. The catalysts are suitable for producing hydrocarbons from synthesis gas. Supports for the catalysts may be kieselguhr, silica gel, activated alumina and acid-treated clays.

U.S. Pat. No. 4,294,725 to Fraenkel et al. discloses a process for producing hydrocarbons from synthesis gas with a catalyst comprising a transition metal component reduced by the vapor of a metal having an appreciable electromotive series potential difference from the transition metal. The support for the catalyst in this process is preferably a synthetic zeolite 5A or a zeolite of the Faujasite family.

SUMMARY OF THE INVENTION

Our invention is a process for producing isoparaffins from synthesis gas which comprises contacting the synthesis gas with a catalyst comprising a cadmium component and an acidic support component wherein the iso/normal paraffin ratio of butane in the product is greater than about five, and the iso/normal paraffin ratio of pentane in the product is greater than about eight.

The synthesis gas is a mixture of carbon monoxide and hydrogen. The cadmium component is preferably cadmium oxide at about five weight percent CdO. The better acidic support components are rare earth-exchanged X and Y zeolites, ultrastable Y zeolite, cadmium-exchanged Y zeolite and aluminum expanded clay. The catalyst is more selective for the higher-octane isoparaffin products compared to normal paraffin products.

DESCRIPTION OF THE PREFERRED EMBODIMENTS

The raw material for our process is synthesis gas which is a mixture of hydrogen and carbon monoxide. Synthesis gas itself may be made by conventional methods from numerous sources containing carbon, such as coal, natural gas and biomass. Two conventional coal gasification methods, for example, are the well known Lurgi and Sasol processes.

Typically, the mole ratio of carbon monoxide-to-hydrogen in the synthesis gas is within the range of about 1/10 to 10/1. Preferably, the ratio is 1/4 to 2/1. The effect on catalyst activity or product hydrocarbon selectivity of the carbon monoxide-to-hydrogen ratio is minor. Best results were obtained when the ratio was about 1/1.

Additionally, the synthesis gas may contain other components, both reactive and unreactive. Methane, oxygen and carbon dioxide are some other components which may be in the synthesis gas without adversely affecting the performance of our catalyst. Hydrogen sulfide, however, was found to be a severe poison for our catalyst, and commercial units for our process may require a sulfur guard bed upstream of the catalyst in order to protect it from sulfur compounds.

Our catalyst is a solid, porous contact mass with several components; a cadmium component and an acidic support component. Our contact mass may be in the form of numerous loose pellets, chips or spheres. Or, it may be one solid, porous mass.

The cadmium component can be present either as a component deposited on the support or as a component formed from cadmium ions exchanged into the support replacing exchangeable cations in the support. The cadmium component is in the form of elemental cadmium, its oxide or salt or a combination thereof, and is present at a concentration level in the range of from about 0.1 to about 20 weight percent, calculated as cadmium oxide and based on the weight of the catalyst. Preferably the cadmium component is present at a concentration level of from about 1 to about 10 weight percent. The cadmium component is preferably in the form of cadmium oxide.

The acidic support component may be any porous support material having strong acidic properties. Thus, suitable supports comprise a zeolite or a molecular sieve, a pillared smectite or vermiculite clay, or a combination thereof.

The acidic support material of the catalyst employed in the method of the present invention can also comprise a zeolite crystalline molecular sieve containing exchangeable cations and can be in the unexchanged or cation-exchanged form. A suitable molecular sieve comprises a crystalline aluminosilicate, crystalline borosilicate or a combination thereof. A suitable crystalline aluminosilicate includes chabazite, clinoptilolite, erionite, mordenite, zeolite A, zeolite L, zeolite X, zeolite Y, ultrastable large-pore zeolite Y, zeolite omega, or a ZSM-type zeolite such as ZSM-5, ZSM-11, ZSM-12, ZSM-35, ZSM-38 or ZSM-48.

Another example of a crystalline molecular sieve that can be employed in the support of the catalyst employed in the method of the present invention is a metal-exchanged, Y-type molecular sieve. Y-type, zeolitic molecular sieves are discussed in U.S. Pat. No. 3,130,007. The metal-exchanged, Y-type molecular sieve can be prepared by replacing the original cation associated with the molecular sieve by a wide variety of other cations according to techniques that are known in the art. Ion exchange techniques have been disclosed in many patents, several of which are U.S. Pat. Nos. 3,140,249; 3,140,251; and 3,140,253. Specifically, a mixture of rare earth metals can be exchanged into a Y-type zeolitic molecular sieve, and such rare earth metal-exchanged, Y-type molecular sieve can be employed suitably in a support used in the catalyst employed in the method of the present invention. Specific examples of suitable rare earth metals are cerium, lanthanum, and praesodymium. In one particularly preferred embodiment, cadmium ions are exchanged into a Y-type zeolitic molecular sieve, with the result being that the cadmium component of the catalyst is a component of the catalyst support.

Ultrastable, large-pore, Y-type, zeolitic crystalline aluminosilicate material is described in U.S. Pat. Nos. 3,293,192 and 3,449,070. Each of these patents is specifically incorporated by reference herein. By large-pore material is meant, a material that has pores which are sufficiently large to permit the passage thereinto of benzene molecules and larger molecules and the passage therefrom of reaction products.

The acidic support component may also be pillared smectite and vermiculite clays, which are also often referred to in the literature as pillared interlayered clays and occasionally as molecular sieves. The smectite clays comprise montmorillonite, beidellite, montronite, volchonskoite, hectorite, saponite, stevensite, sauconite and pimelite.

Preferably, when the support comprises an aforesaid zeolite or molecular sieve material or an aforesaid pillared smectite or vermiculite clay material or a combination thereof, the support also comprises an aforesaid amorphous refractory inorganic oxide. In such cases, the concentrations of the amorphous inorganic oxide and of the zeolite or molecular sieve material and/or pillared smectite or vermiculite clay material are not critical. Preferably, the amorphous refractory inorganic oxide content is at least high enough to be effective to give the support sufficient strength and integrity so that the ultimate catalyst composition can be employed in the method of the present invention without appreciable damage to the catalyst. In such case, the total concentration of the zeolite molecular sieve material and/or pillared smectite or vermiculite clay material in such mixture is preferably from 5 to 90 weight percent, more preferably from 20 to 60 weight percent, based on the weight of the support, which support is made up of the amorphous refractory inorganic oxide and the zeolite or molecular sieve material and/or the pillared smectite or vermiculite clay material.

The catalysts employed in the method of this invention can be prepared by impregnation of an aforesaid suitable support with at least one precursor of the cadmium component. Any convenient conventional impregnation technique can be employed for this purpose. For example, when the support comprises an amorphous refractory inorganic oxide and a zeolite or molecular sieve and/or a pillared smectite or vermiculite clay, numerous convenient impregnation techniques can also be employed. For example, finely-divided zeolite or molecular sieve material and/or pillared smectite or vermiculite clay material can be stirred into a sol or gel of a refractory inorganic oxide, and at least one soluble compound of cadmium is added to the sol or gel, followed by co-gelling of the sol or gel mixture by the addition of dilute ammonia. The resulting co-gelled material is then dried and calcined.

It is, of course, also suitable to impregnate only one of the amorphous refractory inorganic oxide, the molecular sieve material or pillared smectite or vermiculite clay material in the mixture, or to impregnate each of the aforesaid amorphous inorganic oxide, molecular sieve material and/or pillared smectite or vermiculite oxide and molecular sieve material and/or pillared smectite or vermiculite clay material. Thus, it is contemplated that, if the catalyst employed in the method of this invention comprises an amorphous refractory inorganic oxide and at least one of a molecular sieve material and a pillared smectite or vermiculite clay material, the cadmium component can be deposited on only one, only two, or all of the components of the support.

In each of the above preparations involving a zeolite or molecular sieve material, the material employed can be either in its unexchanged form or in its ion-exchanged form. Preferably, the zeolite or molecular sieve material is one which has previously been cation-exchanged. A suitable cation-exchange procedure comprises making a slurry of the material in a solution of a cation, such as ammonium ions, which is to be exchanged with the alkali metal in the zeolite or molecular sieve material, stirring the slurry at a temperature of about 100° C. for at least about two hours, filtering the slurry, washing the filtered solid with distilled water, and drying and calcining the solid. It is also suitable to incorporate the presursor of the cadmium component into the molecular sieve by cation exchange using a conventional ion exchange procedure. Thus, the cadmium component can be incorporated into the molecular sieve support itself, in addition to or instead of being deposited on the surface of the molecular sieve support.

EXAMPLE 1

Several catalysts were evaluated to determine the effect of the acidic support on hydrocarbon selectivity.

Catalyst supports were prepared using an alumina sol obtained from American Cyanamid and the appropriate zeolite. For example, 340 g of alumina sol (10.3% aluminum oxide) was mixed thoroughly in a blender with 15.0 g of a rare-earth-exchanged Y zeolite. The alumina was geled by the rapid addition of a 10% ammonium hydroxide solution. The mixture was dried at 120° C. and calcined at 540° C. for 3 hours. Similar catalyst supports were made with ultrastable (US) Y zeolite, mordenite, ZSM-5, and rare-earth-exchanged X zeolites. Supports also were made with a cadmium-exchanged sodium Y zeolite and with an alumina-expanded bentonite clay.

A suspension of 400 grams of a bentonite, 90 weight percent of which is montmorillonite (supplied by American Colloid Company and designated Volclay 325), in 227 cubic centimeters of water was mixed with 304 grams of a 50 weight percent solution of Reheis alumina Chlorhydrol, and the pH of the resulting suspension was adjusted to 4 with ammonium hydroxide. The suspension was heated at 72° C. for 1 hour and then filtered, and the resulting separated solid was washed with water, dried at 100° C. and calcined at 500° C. for 2 hours.

30.27 grams of this composition was combined with 221.5 grams of an alumina sol containing about 9 weight percent of alumina, and 10 grams of an aqueous solution containing about 28 weight percent of ammonium hydroxide was added to gel the resulting mixture. The resulting gel was dried at 120° C. and calcined at 540° C. for 6 hours. The resulting composition contained 60 weight percent of the alumina-expanded smectite clay and 40 weight percent of alumina.

Cadmium was incorporated by the method or incipient wetness. The pores of the support were filled with an aqueous solution of cadmium nitrate. For example, to 20.0 g of 30% rare earth (RE) Y zeolite dispersed in an alumina matrix was added 3.00 g of $Cd(NO_3)_2.4H_2O$ dissolved in 10 ml of water and mixed well. After standing for 1 hour, the catalyst was dried overnight in an oven at 120° C. and for an additional 3 hours in a furnace at 540° C.

Catalysts were crushed to particles passing 12-mesh screens and retained on 20-mesh screens (US standard) and then placed in a reactor and pressurized with a mixture of carbon monoxide and hydrogen. Cadmium catalysts do not require any special activation procedure.

Typically, 5.0 g of catalyst was reacted with syngas in either of two small catalyst testing units—one with a Berty reactor (500 cc) and the other with a fixed-bed, plug-flow tubular reactor (0.95 cm i.d.). The Berty reactor is a back-mixed reactor in which the flow into reactor of each of carbon monoxide and hydrogen was controlled individually. To start a run, 5 grams of the particular catalyst used was loaded into the reactor, and reactor was closed. The pressure of the reactor was then raised to the desired level by introducing carbon monoxide and hydrogen. The temperature of the reactor was then raised to the desired level. Products and unreacted reactants passed continuously out of the reactor. The plug-flow tubular reactor has a diameter of 0.95 centimeter and 63.5 centimeters long and contains a bed of about 5.0 grams of catalyst. A premixed mixture of carbon monoxide and hydrogen was introduced through one end of the plug-flow reactor, and reactor effluent was withdrawn from the other end of the reactor. The gas introduced to the reactor was used to pressure the reactor to the desired level.

With both testing units, gas concentrations and product analysis were determined by two gas chromatographs in series with the reactor. The inlet flow rate for both hydrogen and carbon monoxide were regulated by electronic mass flow controllers. The outlet flow rate was measured by a conventional wet test meter. The outlet gas flow rate, carbon monoxide, and carbon dioxide concentrations were determined first with the reactor at room temperature. After the catalyst was heated to reaction temperature, the outlet gas flow rate, carbon monoxide, and carbon dioxide concentrations were again determined. The carbon monoxide conversion was computed by difference. Generally, the carbon mass balance was $100\pm5\%$.

Each catalyst, containing 5% CdO on a different acidic support was tested at 400° C. and 34 atm using syngas with a hydrogen to carbon monoxide ratio of 2/1. The results of tests conducted in the Berty reactor are shown in Table 1. In this table, selectivities for methane by all catalysts is high because of the high reaction temperature. However, several trends are noticeable. Highly acidic, high aluminum zeolites result in catalysts that give lower methane selectivity and a higher selectivity for $C_4$ to $C_7$ isoparaffin products. The catalyst supports in order of decreasing selectivity for $C_4$ to $C_7$ isoparaffins are REY, US Y>Al bentonite clay, Cd-Y>H mordenite>>H-ZSM-5. Although not shown in Table 1, catalysts that give the highest selectivities of $C_4$ to $C_7$ isoparaffin also give higher yields of hydrocarbon. That is, catalyst activity decreased in the order REY, US Y>H mordenite>>H-ZSM-5, for example. The best supports for both high activity and selectivity for isobutane and higher isoparaffins are REY and US Y zeolites dispersed in an alumina matrix. For most catalysts, zeolite levels of approximately 30% give good activity and selectivity for isoparaffins.

TABLE 1

THE EFFECT OF ZEOLITE STRUCTURE ON HYDROCARBON SELECTIVITY[a]

| | Catalyst: | | |
|---|---|---|---|
| | 5% CdO on 30% REY zeolite 70% alumina | 5% CdO on 30% USY zeolite 70% alumina | 5% CdO on 60% Al bentonite 40% alumina |
| | Feed rate cc gas/h/g cat: | | |
| | 600 | 1100 | 2000 |
| Hydrocarbon products, wt % | | | |
| Methane | 24 | 27 | 28 |
| Ethane | 2 | 6 | 7 |
| Propane | 19 | 4 | 11 |
| Propene | 1 | 6 | 1 |
| Isobutane | 27 | 16 | 19 |
| n-Butane | 6 | 2 | 4 |
| Isopentane | 10 | 13 | 9 |
| n-Pentane | 1 | 1 | 1 |
| Isohexane | 5 | 9 | 5 |
| n-Hexane | t | 1 | 1 |
| Heavier paraffins | 5 | 15 | 14 |

| | Cd-exchanged 5% CdO on | 5% CdO on | |
|---|---|---|---|
| | Catalyst: | | |
| | 30% Y zeolite 70% alumina 1500 | 20% H mordenite 80% alumina 1000 | 60% ZSM-5 40% alumina 2008 |
| Hydrocarbon products, wt % | | | |
| Methane | 54 | 60 | 85 |
| Ethane | 4 | 7 | 13 |
| Propane | 6 | 19 | 1 |

TABLE 1-continued

THE EFFECT OF ZEOLITE STRUCTURE ON HYDROCARBON SELECTIVITY[a]

| | | | |
|---|---|---|---|
| Propene | 2 | t[b] | — |
| Isobutane | 12 | 2 | t |
| n-Butane | 2 | 3 | — |
| Isopentane | 7 | 3 | t |
| n-Pentane | 1 | t | — |
| Isohexane | 5 | 1 | — |
| n-Hexane | t | 1 | — |
| Heavier paraffins | 8 | 6 | 1 |

[a] Berty reactor at 34 atm, 400° C., H/CO = 2:1.
[b] t, trace

EXAMPLE 2

Among the best catalysts, only minor differences in isoparaffin selectivity were observed. For example, in a tubular plug-flow reactor, REX-supported catalysts, which are similar to REY-supported catalysts, give slightly higher selectivities of isopentane and isohexane, while REY-supported catalysts give higher selectivities for isobutane (Table 2). For all cadmium catalysts, the iso/normal ratio for butane is greater than five, and the iso/normal ratio for pentane is greater than eight.

EXAMPLE 3

Under some reaction conditions, supported cadmium oxide is reduced to cadmium metal, and some cadmium is lost from the catalyst support and is deposited on the reactor walls. The amount of cadmium lost by reduction of cadmium oxide to cadmium metal is dependent on the acidity of the catalyst support and the cadmium level on the catalyst. For example, we noticed in our work that little or no cadmium is lost from amorphous, acidic silica-alumina support, while large amounts of cadmium oxide are reduced and volatilized as cadmium metal from weakly acidic materials, such as alumina. The following experiments demonstrate the reduction and loss of cadmium from an alumina-supported cadmium oxide. Equal amounts of a 5% cadmium oxide on alumina catalyst (14/20 mesh) and a cadmium-free 50 wt% ultrastable Y zeolite in an alumina matrix (⅛ in. extrudate) were added to a non-flow autoclave reactor. The reactor was pressurized with one part carbon monoxide and two parts hydrogen, and the reactor was heated to 425° C. The reactor pressure was maintained at 70 atm. After 96 hours, the reactor was depressurized, cooled, and the catalysts were removed and separated. The extrudates containing the zeolites, which initially contained no cadmium, were now found to contain 1.8% cadmium. The experiment was repeated with equal amounts cadmium-exchanged Y zeolite in an alumina matrix (14 to 20 mesh) and a cadmium-free 50 wt% ultrastable Y zeolite in an alumina matrix (⅛ inch extrudate). In this experiment, no cadmium migrated to the ultrastable Y zeolite from the cadmium-exchanged Y zeolite. In both experiments, isoparaffins were formed in high yields.

TABLE 2

Conversion of Syngas to Hydrocarbons with 5% CdO on 30% Rare-Earth-Exchanged Zeolite/70% Alumina[a]

| Catalyst zeolite type: | REY | | REX | |
|---|---|---|---|---|
| Inlet gas composition: | | | | |
| Hydrogen | 64% | | 65% | |
| Carbon monoxide | 34% | | 33% | |
| Carbon dioxide | 2% | | 2% | |
| Temperature, °C. | 350 | 360 | 350 | 360 |
| Total CO Conversion, % | 27 | 33 | 29 | 34 |
| CO converted to CO$_2$, % | 10 | 13 | 12 | 15 |
| CO converted to product, % | 17 | 20 | 17 | 19 |
| Hydrocarbon products, wt % | | | | |
| Methane, ethane, propane | 9 | 12 | 6 | 9 |
| Butanes | 43 | 37 | 24 | 27 |
| Pentanes | 21 | 18 | 38 | 19 |
| Heavier paraffins | 30 | 30 | 32 | 45 |
| Hydrocarbon yield, g/h/g cat | 0.072 | 0.085 | 0.071 | 0.082 |

[a] Tubular reactor; total pressure: 68 atm; Feed rate: 2100 cc/h/g catalyst.

These experiments demonstrate that cadmium oxide on alumina is easily reduced to volatile cadmium metal by mixtures of hydrogen and carbon monoxide and is lost from the alumina under typical conditions for hydrocarbon synthesis. Cadmium ion-exchanged into a zeolite, however, is not lost under similar conditions. Perhaps, strongly acid supports can retain the volatile cadmium by oxidation of cadmium metal by the acidic support. For many of the zeolite catalysts, it is not necessary to exchange cadmium directly into the zeolite but only that cadmium be associated with an acidic support. In the absence of an acidic support, cadmium oxide, cadmium metal, and other cadmium compounds did not catalyze carbon monoxide reactions.

EXAMPLE 4

A solution containing 3 grams of Cd(NO$_3$)$_2$.4H$_2$O in 14 milliliters of water was combined and blended for 1 hour with 23.75 grams of gamma alumina (from Continental Oil Company and designated Catapal) having a pore volume of 0.65 cubic centimeter per gram, a surface area of 200 square meters per gram, and average pore diameter of 130 angstroms, and a particle size of 0.16 centimeter. The blend was dried at 120° C. for 1 hour and calcined at 540° C. in air for 1 hour. The resulting catalyst contained 5 weight percent of cadmium oxide, based on the weight of the catalyst.

When this catalyst was tested in the plug-flow reactor at 344° C., 34 atm and a gas feed rate of 1500 cc/hour/gram, the product contained no isoparaffins. Rather, the product was 29% methane, 11% methanol and 60% dimethylether.

EXAMPLE 5

A catalyst composition of 5% cadmium oxide, supported on a matrix of 30% rare-earth-exchanged Y zeolite dispersed in an aluminum matrix, was used for more extensive experiments to determine the range of reaction conditions for synthesizing isoparaffins from syngas.

Isoparaffin synthesis with the catalyst was investigated over a temperature range from 315° to 400° C. Hydrocarbon yields increase with increasing temperature, although methane, $C_2$, and $C_3$ selectivity also increased with increasing temperature. The temperature where hydrocarbon synthesis gives high yields of $C_4$ to $C_7$ isoparaffins and minimizes $C_1$ to $C_3$ yields is near 360° C.

At reaction pressures of 10 atm, only traces of hydrocarbon and carbon dioxide products are obtained. Above 20 atm, however, yields of isoparaffins and carbon dioxide products increase with increasing reaction pressure. Hydrocarbon distributions were only slightly affected by reaction pressure.

Gas rates (total carbon monoxide and hydrogen) of 1400 and 2800 cc/hour/gram catalyst were examined for their effect on isoparaffin synthesis. The higher gas rate increased hydrocarbon yield. A larger increase in hydrocarbon yield with high gas rate was observed at 68 atm, while a modest increase in hydrocarbon yield was obtained at 34 atm. At reaction pressures of 34 and 68 atm, the carbon dioxide yield was approximately inversely proportional to the gas flow rate. High gas flow rates were the most effective way of limiting carbon dioxide formation.

The gas composition has a minor effect on catalyst activity or product hydrocarbon selectivity. With a hydrogen to carbon monoxide ratio of 1/1, the hydrocarbon yields were approximately 10% higher than with a 2/1 hydrogen to carbon monoxide ratio. Sulfur was found to be a severe poison for cadmium syngas catalysts. Addition of $H_2S$ to the feed resulted in the irreversible formation of CdS which was catalytically inactive.

In summary, isoparaffins were selectively produced at reaction pressures above 20 atm, temperatures from 315° to 400° C. with gas rates of 1400 to 2800 cc/hour/gram catalyst, and with hydrogen to carbon monoxide ratios from 2/1 to 1/1. Yields of isoparaffins ranged from traces of products at 10 atm up to 0.1 g/h/g catalyst at higher reaction pressures and gas rates. High gas rates reduce the carbon dioxide formed during the synthesis reactions. For this catalyst, no aromatic or oxygenated products were obtained at any of the process conditions. At these reaction conditions, cadmium catalysts are stable. Tests show no significant loss in activity or changes in product selectivities over a period of 30 days.

The Examples show that cadmium oxide catalysts on acidic supports are highly reactive for the conversions of hydrogen and carbon monoxide to saturated, low molecular weight isoparaffins. Catalyst activity and selectivity are functions of catalyst composition and process conditions. For isoparaffin formation, active catalysts require two components. First, active catalysts contain approximately 5% cadmium oxide, which converts carbon monoxide to reactive intermediates, possible methanol and dimethyl ether. Second, to stabilize the cadmium ion in a catalytically active state, an acidic support is required: for example, a zeolite, an expanded clay, or even amorphous silica-alumina. Although the product distribution is dependent on the type of acid component, the hydrocarbon products are characterized by a distribution of $C_1$ to $C_7$ paraffins. In addition, most of the $C_4$ to $C_7$ hydrocarbons are isoparaffins. Olefins in the products are low, generally under 10%. Under optimum conditions, methane yields are low, and isobutane and isopentane are the predominant products. At reaction pressures above 20 atm, temperatures from 315° to 400° C., synthesis gas rates between 1400 and 2800 cc/h/g catalyst, and hydrogen to carbon monoxide ratios from 2/1 to 1/1, the ratio of isobutane to normal butane in the product is greater than about five, and the ratio of isopentane to normal pentane in the product is greater than about eight. No aromatic hydrocarbons or oxygenates, other than methanol and dimethyl ether, were detected. The preferred catalysts for producing isoparaffins from syngas are cadmium oxide supported on faujasite or aluminum-expanded clays.

What we claim is:

1. A process for producing isoparaffins from synthesis gas which comprises contacting the synthesis gas with a catalyst comprising a cadmium component and an acidic support component wherein the iso/normal paraffin ratio of butane in the product is greater than about five, and the iso/normal paraffin ratio of pentane in the product is greater than about eight when the catalyst is tested at reaction pressures above 20 atm, temperatures from 315° to 400° C., synthesis gas rates between 1400 and 2800 cc/h/g catalyst, and hydrogen to carbon monoxide ratios from 2/1 to 1/1.

2. The process of claim 1 wherein the catalyst comprises about 5 weight percent cadmium oxide.

3. The process of claim 1 wherein the acidic support material is rare-earth-exchanged Y zeolite and alumina.

4. The process of claim 1 wherein the acidic support material is rare-earth-exchanged X zeolite and alumina.

5. The process of claim 1 wherein the acidic support material is ultrastable Y zeolite and alumina.

6. The process of claim 1 wherein the acidic support material is aluminum-expanded bentonite clay.

7. The process of claim 1 wherein the acidic support material is cadmium-exchanged Y zeolite and alumina.

8. The process of claim 1 wherein the acidic support material is H mordenite and alumina.

9. The process of claim 1 wherein the acidic support material is amorphous silica-alumina.

* * * * *